United States Patent [19]

Barberet-Maiolino et al.

[11] Patent Number: Plant 7,048

[45] Date of Patent: Oct. 17, 1989

[54] SPRAY CARNATION NAMED LONDUCI

[75] Inventors: Nicole Barberet-Maiolino; Henri Blanc, both of Antibes, France

[73] Assignee: Establissements: Barberet et Blanc Laboratoire de Physiologie Vegetale, Les-Maures, France

[21] Appl. No.: 255,482

[22] Filed: Oct. 11, 1988

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new spray carnation variety particularly distinguished by its dark red flowers of relatively small size produced profusely on strong, erect stems of medium length growing on a vigorous, upright plant having moderately abundant foliage and reaching an average height of about 106 cm. at eight months of growth. This plant has strong resistance to *Fusarium oxysporum.*

1 Drawing Sheet

BACKGROUND OF THE NEW PLANT

This new spray carnation plant originated in 1986 as a sport of the variety 'Lontoyo' being grown in our nursery at 83250 La Londe-Les-Maures, France, this sport attracting our attention because of its relatively small, bright red flowers borne on strong, upright stems of medium length. Because of its apparently advantageous growth and blooming habit, we selected this sport for propagation, which we did at La Londe by means of cuttings with considerable success. Subsequently this new plant was propagated through several successive generations at La Londe by means of cuttings of successive plants, which demonstrated that the distinctive characteristics of this new variety would hold true from generation to generation and appeared to be firmly fixed so that its homogeneity could be assured.

DESCRIPTION OF THE DRAWING

This new spray carnation is illustrated by the accompanying photographic drawing, which shows several of the blooming stems bearing buds and flowers in various stages of development, the color rendition being as nearly true to that specified as is reasonably possible to obtain by conventional, professional photographic procedures.

DESCRIPTION OF THE NEW PLANT

The following is a detailed description of our new spray carnation based upon observation of plants growing in Southern France during the Spring of 1988, the color designations being according to The R.H.S. Colour Chart published by The Royal Horticultural Society of London, England.

THE PLANT

Origin: Sport.
Parentage: The cultivar 'Lontoyo'.
Classification:
- *Botanic.*—*Dianthus caryophyllus.*
- *Commercial.*—Spray carnation.

Form: Bush with at least four stems emitted near the ground.
Height: Averages about 106 cm. at eight months.
Main stem length: About 15 cm. due to pinching.
Growth: Vigorous, rigid and upright.

Branching character: Moderate.
Foliage:
- Quantity.—Moderately abundant.
- Number of leaves.—More than 120.
- Leaf size.—About 11 cm. long and 0.7 cm. wide at the seventh node.
- *Leaf shape.*—Oblong with entire margins.
- *Texture.*—Leathery.
- *Color.*—Upper side and under side, Greyed Green, RHS 189-A/B.
- *Ribs.*—Hardly noticeable.
- *Rachis.*—Hardly noticeable.

THE BUD

Size: Small.
- *Diameter.*—About 1 cm., in average.
- *Length.*—About 2.6 cm., in average.

Shape: Cylindrical
Rate of opening: Normal.
Color of petals: When sepals first divide, Turkey Red, RHS 46-C. When petals begin to unfurl, RHS 46-B/C.
Sepals:
- *Number.*—Five.
- *Shape.*—Lanceolate but jointed together at their base.
- *Character.*—The sepals stand up as the flowers open.
- *Color.*—Inside, RHS 145-C. Outside, RHS 144-C and 138-B.
- *Striae.*—Longitudinal striae.

Calyx:
- *Size.*—Long.
- *Shape.*—Cylindrical.
- *Splitting.*—The calyx does not split.
- *Aspect.*—Smooth.

Flower stem: Rigid and erect.

THE INFLORESCENCE

Blooming habit: Recurrent and profusely during Spring, Midseason and Fall with a tendency to give few blooms in Fall.
The flower:
- *Size.*—Small. Diameter — About 5 cm., in average. Depth — About 4.4 cm., in average.
- *Borne.*—In a cluster on strong, upright stems.

*Shape.*—When bloom first opens, high centered. When bloom matures, dome-shaped.

Petalage:

*Number.*—Twenty-nine, in average.

*Arrangement.*—Imbricated.

*Form.*—Fan-shaped and slightly wrinkled at the edges and finely serrated at the apex.

*Texture.*—Leathery.

*Aspect.*—Satiny.

*Color.*—All petals: Body, Turkey Red, RHS 46-B/C. Base, Greenish. Reverse side, RHS 46-C.

Petaloids.—Number: Less than four. Size: Smaller than the petals. Color: The same as the petals.

Flower stem:

*Length.*—About 57 cm., in average, cut at the tenth node.

*Color.*—Greyed Green, RHS 189-A/B.

*Character.*—Upright with good strength.

Discoloration after full bloom: Very little.

Persistence: The flowers hang on and dry.

Fragrance: Strong

Disease resistance: Resistent to *Fusarium oxysporum* as observed I.N.R.A. 06600, Antibes, Frances.

Lasting quality: At least ten days as a cut flower in vase keeping.

REPRODUCTIVE ORGANS

Stamens:

*Number.*—Twelve, in average.

*Arrangement.*—Around the ovary.

*Anthers.*—Size: About 4 mm.

Pistils:

*Number.*—Three or four.

*Styles.*—Color: Reddish.

*Stigmas.*—Color: Reddish.

Character of ovaries: Ribbed.

The foregoing characteristics of this plant can be more-or-less strongly modulated under the environmental conditions where grown, the method of cultivation and the latitude and season where grown.

We claim:

1. The new and distinct spray carnation variety and the parts thereof, substantially as herein shown and described, characterized by the bright red color of its blossoms, its profuse production of flowers during the Spring, Midseason and Fall growing seasons, its abundant foliage, and its strong, rigid and upright growth habit.

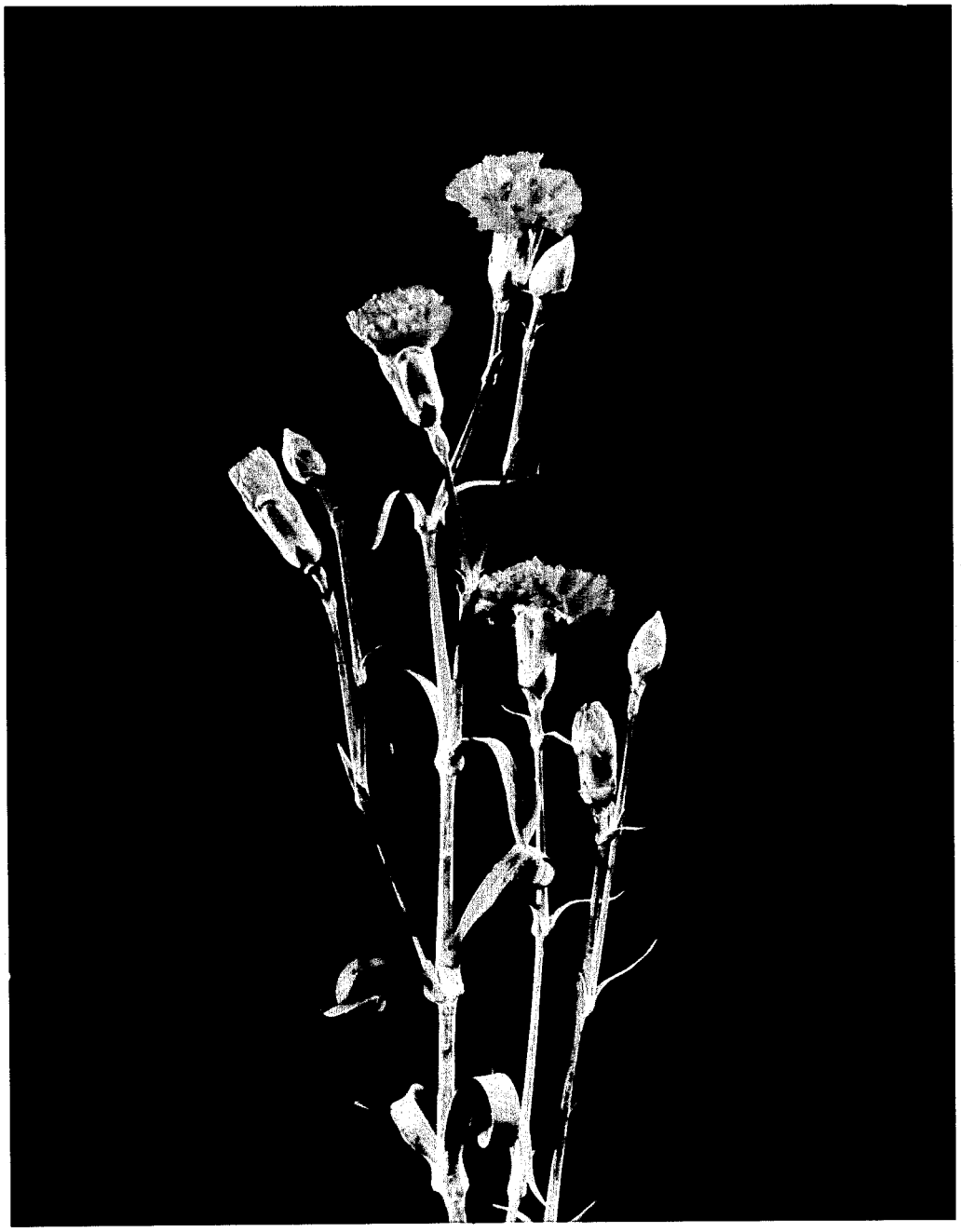

* * * * *